(12) United States Patent
Kubo

(10) Patent No.: US 8,821,177 B2
(45) Date of Patent: Sep. 2, 2014

(54) CONNECTOR MECHANISM

(71) Applicant: Olympus Medical Systems Corp., Tokyo (JP)

(72) Inventor: Takafumi Kubo, Akiruno (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/050,886

(22) Filed: Oct. 10, 2013

(65) Prior Publication Data

US 2014/0094067 A1    Apr. 3, 2014

Related U.S. Application Data

(63) Continuation of application No. PCT/JP2013/063420, filed on May 14, 2013.

(30) Foreign Application Priority Data

Jul. 30, 2012  (JP) .................................. 2012-168534

(51) Int. Cl.

| | |
|---|---|
| *H01R 13/52* | (2006.01) |
| *G02B 23/24* | (2006.01) |
| *A61B 1/04* | (2006.01) |
| *H01R 13/46* | (2006.01) |
| *A61B 1/00* | (2006.01) |
| *H01R 12/71* | (2011.01) |
| *H01R 12/73* | (2011.01) |

(52) U.S. Cl.
CPC ............ *H01R 13/46* (2013.01); *G02B 23/2476* (2013.01); *H01R 12/712* (2013.01); *A61B 1/04* (2013.01); *H01R 12/73* (2013.01); *H01R 13/5219* (2013.01); *A61B 1/00124* (2013.01)

USPC ............................................. 439/271; 439/74

(58) Field of Classification Search
USPC ................. 439/271–273, 74, 66, 75
See application file for complete search history.

(56) References Cited

U.S. PATENT DOCUMENTS

| | | | |
|---|---|---|---|
| 6,334,785 B2 * | 1/2002 | Miwa ............................ 439/272 |
| 6,358,063 B1 * | 3/2002 | Neidich ......................... 439/66 |
| 7,364,433 B2 * | 4/2008 | Neidlein ........................ 439/66 |
| 2001/0027047 A1 * | 10/2001 | Miwa ............................ 439/272 |
| 2004/0121628 A1 * | 6/2004 | Hinata et al. .................. 439/66 |
| 2006/0141870 A1 | 6/2006 | Milbrand, Jr. et al. | |

FOREIGN PATENT DOCUMENTS

| | | |
|---|---|---|
| JP | 2004-327169 A | 11/2004 |
| JP | 2011-146286 A | 7/2011 |

* cited by examiner

*Primary Examiner* — Gary Paumen
(74) *Attorney, Agent, or Firm* — Scully, Scott, Murphy & Presser, P.C.

(57) ABSTRACT

A connector mechanism includes: a first connector that is arranged on a first substrate; a second connector that is arranged on a second substrate and is connected to the first connector in a positional relationship in which the second substrate and the first substrate face each other; and a packing including: a first face that elastically abuts against the first substrate; a second face that is a face on an opposite side to the first face and that elastically abuts against the second substrate; and connector abutting convex portions that are protrusively provided with respect to an inner face of a connector space that is a through-hole which allows the first face and the second face to communicate and sealingly houses the connectors in a connected state, and that elastically abut against an outer face of the connectors disposed in the connector space and are disposed integrally with the connectors.

9 Claims, 5 Drawing Sheets

CONNECTOR MECHANISM

CROSS REFERENCE TO RELATED APPLICATION

This application is a continuation application of PCT/JP2013/063420 filed on May 14, 2013 and claims benefit of Japanese Application No. 2012-168534 filed in Japan on Jul. 30, 2012, the entire contents of which are incorporated herein by this reference.

BACKGROUND OF THE INVENTION

1. Field of the Invention

The present invention relates to a connector mechanism that, in a state in which one connector that is arranged on one substrate and another connector that is arranged on another substrate are electrically connected, retains the connectors in a watertight manner.

2. Description of the Related Art

In electronic equipment and the like, connectors are used to electrically connect wiring and circuit boards or to electrically connect circuit boards to each other and the like. In some cases wiring and circuit boards and the like are directly connected to achieve miniaturization and thinning of electronic equipment and the like.

To improve the image quality in electronic endoscopes that are used in medical fields, industrial fields and the like, the number of pixels of image pickup devices of such endoscopes has been increasing. For example, by providing a relay substrate that amplifies a drive signal of an image pickup device inside an operation portion of an endoscope, in addition to improving the image quality, the diameter of an image pickup cable that is inserted through the inside of the insertion portion is also reduced.

In the aforementioned endoscope, in consideration of the repairability and assemblability and the like, a substrate to which an image pickup cable is connected and a relay substrate are electrically connected by a connector inside an operation portion. The substrate to which the image pickup cable is connected and the relay substrate are electrically connected inside the operation portion of the endoscope that is a watertight structure. However, in the event of water or the like entering into the operation portion, a malfunction will occur at an electrical connection portion. Consequently, it is desirable for an electrical connection portion that is formed by connectors to be retained in a watertight state.

The electrical connection portion, for example, is constituted by connecting a male connector that is mounted on the relay substrate and a female connector that is mounted on the substrate that is connected to the image pickup cable (hereunder, referred to as "cable substrate"). The watertightness of a connector connection portion that is the electrical connection portion is maintained by means of a packing.

The packing is disposed so as to surround an outer shape forming portion of the connector connection portion, and in this disposed state, one face of the packing is crushed by a flat face of the relay substrate and adheres thereto, and another face of the packing is crushed by a flat face of the cable substrate and adheres thereto. As a result, the connector connection portion is sealingly housed in a space inside the packing. Because the connector connection portion is sealingly housed inside the packing, a problem is prevented whereby drops of water or the like enter the electrical connection portion at a time of assembly, a time of repair, or when using the endoscope.

Note that Japanese Patent Application Laid-Open Publication No. 2011-146286 discloses a waterproof attachment structure of a substrate connecting connector. Further, Japanese Patent Application Laid-Open Publication No. 2004-327169 discloses a packing that is miniaturizable and is capable of surely waterproofing an area between articles, as well as a connector that includes the packing.

SUMMARY OF THE INVENTION

A connector mechanism according to one aspect of the present invention includes: a first connector that is arranged on one flat face of a first substrate; a second connector that is arranged on one flat face of a second substrate and is electrically connected to the first connector in a positional relationship in which the one flat face of the second substrate and the one flat face of the first substrate face each other; and a packing having: a first face that elastically abuts against the one flat face of the first substrate; a second face that is a face on an opposite side to the first face and that elastically abuts against the one flat face of the second substrate; and a plurality of connector abutting convex portions that are protrusively provided with respect to an inner face of a connector space that is a through-hole which allows the first face and the second face to communicate and sealingly houses the connectors in a connected state, and that elastically abut against an outer face of the connectors that are disposed in the connector space and are disposed integrally with the connectors.

DETAILED DESCRIPTION OF THE PREFERRED EMBODIMENT

An embodiment of the present invention is described hereunder with reference to the drawings.

One embodiment of the present invention will now be described referring to FIG. 1 to FIG. 6.

Figure 1:
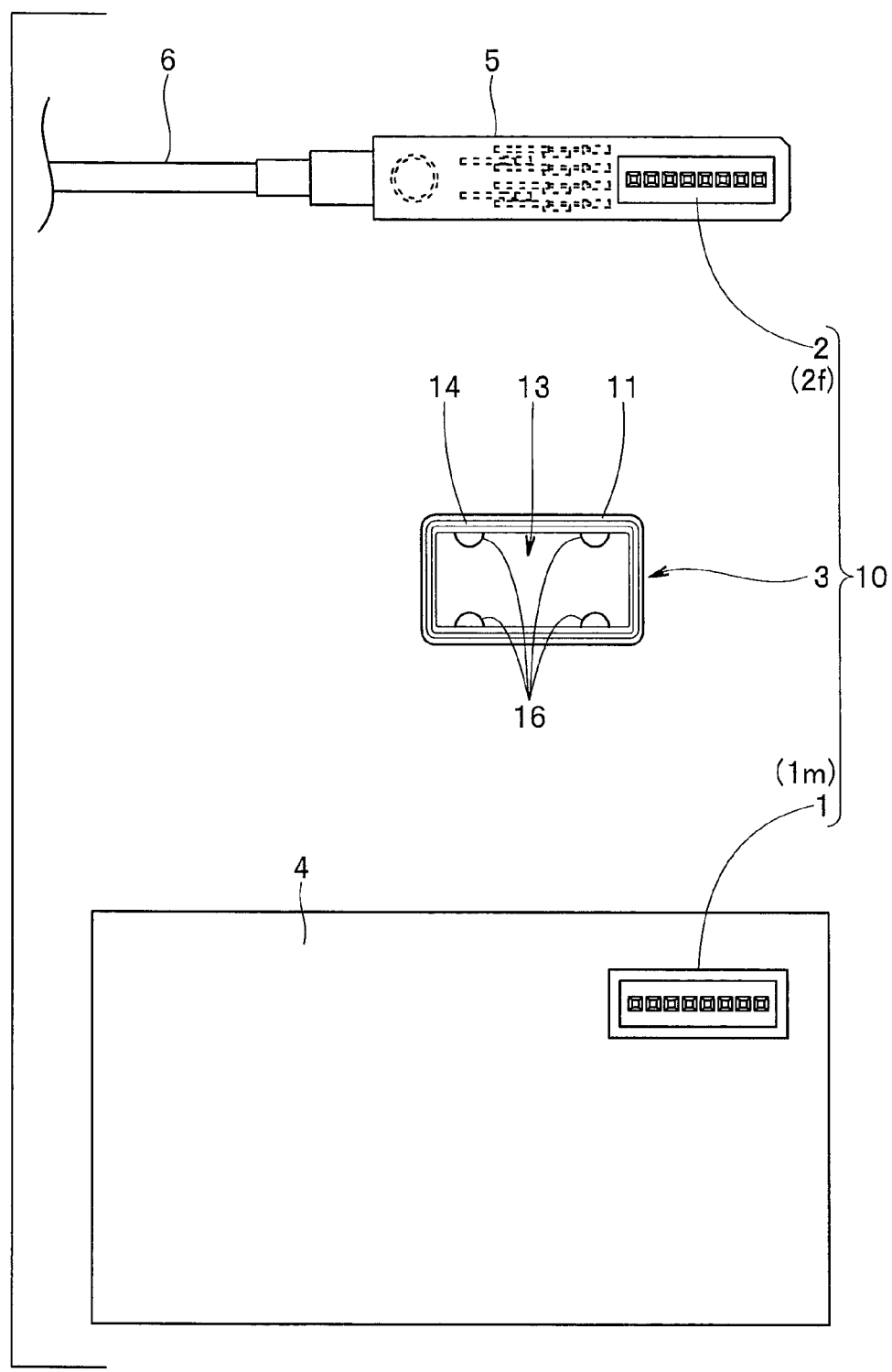
FIG. 1 is a view illustrating a configuration example of a connector mechanism.

As shown in FIG. 1, a connector mechanism 10 includes a first connector 1, a second connector 2, and a packing 3. The first connector 1 is, for example, a rectangular male connector 1m that is mounted at a predetermined position on one flat face of a first substrate 4. The first substrate 4 is a rigid substrate that is set to predetermined dimensions. Various kinds of electronic components that are not shown in the drawings that constitute various kinds of circuits are mounted on the first substrate 4.

The second connector 2 is, for example, a rectangular female connector 2f that is mounted on one flat face of a second substrate 5. The second substrate 5 is a rigid substrate that is set to predetermined dimensions. The second substrate 5 includes a wiring pattern that is not shown in the drawings. The second substrate 5 is electrically connected to, for example, one end of a signal wire 6.

A configuration is adopted with respect to the male connector 1m and the female connector 2f so that the one flat face of the first substrate 4 and the one flat face of the second substrate 5 face each other, and the male connector 1m and the female connector 2f are electrically connected in a predetermined positional relationship.

Note that the aforementioned first substrate 4 and second substrate 5 are not limited to a rigid substrate, and may be constituted by a so-called flexible printed board.

Figure 2A:
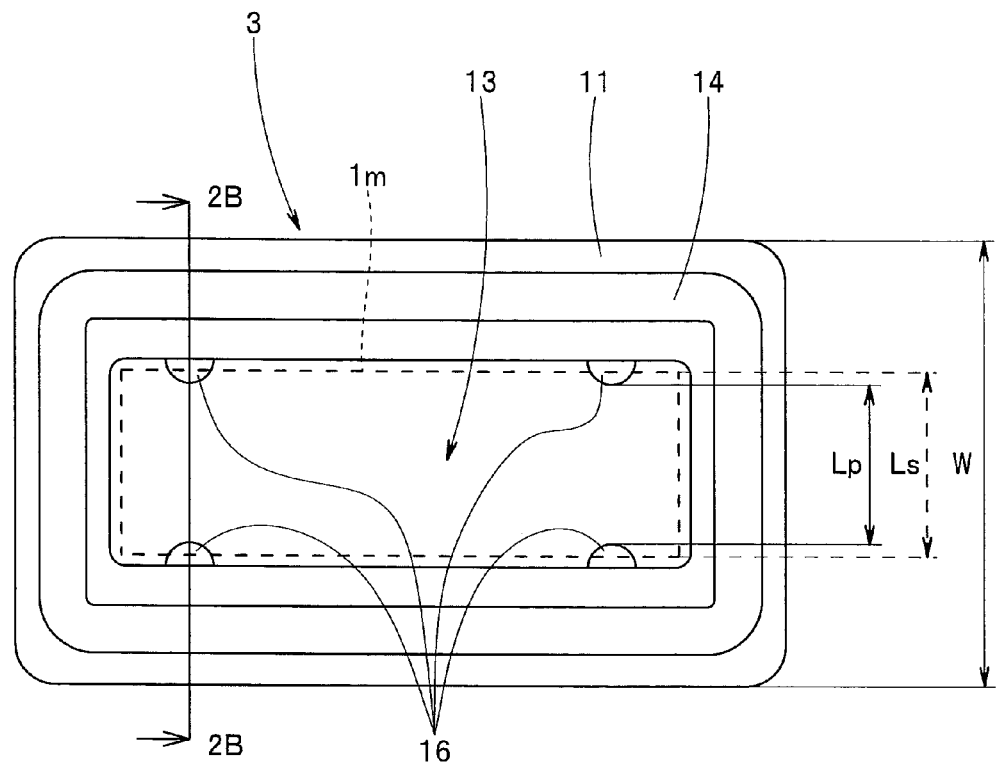
FIG. 2A is an enlarged view of a packing.
Figure 2B:
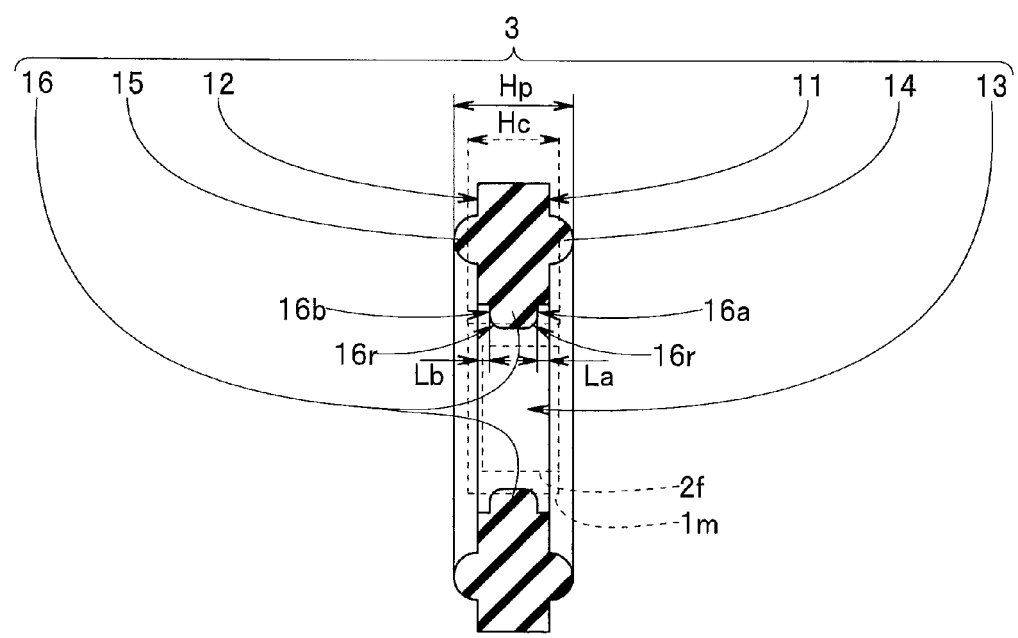
FIG. 2B is a cross-sectional view along a line 2B-2B indicated by arrows in FIG. 2A, and is a view illustrating the relationship between the packing and a connector.

The packing 3 that is shown in FIG. 1, FIG. 2A, and FIG. 2B, for example, is silicon rubber having a predetermined rubber hardness, and is constructed in a predetermined shape.

In the present embodiment, the packing 3 is a rectangular parallelepiped shape, and includes a first face 11, a second face 12, a through-hole 13, a first sealing convex portion 14, a second sealing convex portion 15, and a plurality of connector abutting convex portions 16.

The first face 11, for example, is a flat face that is disposed facing the one flat face of the first substrate 4. The second face 12, for example, is a flat face that is disposed facing the one flat face of the second substrate 5. The through-hole 13 is a hole for constituting a connector space for housing, in a water-tight manner, the connectors 1m and 2f that are in a connected state. The through-hole 13 allows the first face 11 and the second face 12 to communicate with each other.

As shown in FIG. 2A, in the present embodiment an inner face shape of the through-hole 13 is a similar shape to the outer shape of the male connector 1m that is shown by a broken line. That is, a through-hole cross-sectional shape in a direction orthogonal to the axis of the through-hole 13 of the packing 3 is a rectangular shape. A long side of the rectangular-shaped through-hole 13 is set to be larger by a predetermined amount than an outer long side of the male connector 1m. Further, a short side of the through-hole 13 is set to be larger by a predetermined amount than an outer short side of the male connector 1m.

The connector abutting convex portions 16 are provided in a facing positional relationship on facing inner faces including the long sides of the through-hole 13. In the present embodiment, two of the connector abutting convex portions 16 are provided on each inner face. The connector abutting convex portions 16 are configured as, for example, semicircular convex portions that protrude by a predetermined amount from the inner faces which are flat faces.

Note that the number of the connector abutting convex portions 16 that are provided on the inner faces is not limited to two, and may be one or may be more than two. The plurality of connector abutting convex portions 16 are arranged in the long side direction. Further, the respective connector abutting convex portions 16 are not limited to a semicircular convex portion, and may be a quadrangular convex portion, a convex portion with a curved surface shape, or the like. The connector abutting convex portions 16 may also be disposed on the short sides of the packing 3, and not just arranged in the long side direction.

In the present embodiment, the connector abutting convex portions 16 of the packing 3 are elastically deformable. In the packing 3, a distance from the distal end face of the connector abutting convex portion 16 on one inner face side to the distal end face of the connector abutting convex portion 16 on the other inner face side is represented by Lp. The distance Lp is set to be smaller by predetermined dimension than a length Ls of the outer short side of the male connector 1m. An amount of collapse (also described as "rate of collapse") is set with respect to the respective connector abutting convex portions 16 so that the connector abutting convex portions 16 are crushed a predetermined amount by a predetermined amount of force.

In the present embodiment, it is possible to elastically deform the connector abutting convex portions 16 to dispose the male connector 1m with the outer short side length Ls between the connector abutting convex portions 16 on one inner face side and the connector abutting convex portions 16 on the other inner face side that have the distance Lp therebetween.

In this disposed state, the outer face of the male connector 1m is subjected to a pressing force by the elastic forces of the respective connector abutting convex portions 16. That is, the configuration of the packing 3 is capable of stably holding the outer face of the male connector 1m by means of a predetermined elastic force.

As shown in FIG. 2B, in the present embodiment a first convex-portion end face 16a and a second convex-portion end face 16b that are constituted by, for example, a flat face are formed in each connector abutting convex portion 16. The first convex-portion end face 16a is provided at a position that is separated by a predetermined distance (La) from the first face 11. The second convex-portion end face 16b is provided at a position that is separated by a predetermined distance (Lb) from the second face 12. The distance La from the first face 11 to the first convex-portion end face 16a and the distance Lb from the second face 12 to the second convex-portion end face 16b are set to be equal.

As a result, the first face 11 of the present embodiment is configured as a flat face that can be disposed facing one flat face of the first substrate 4, and also as a flat face that can be disposed facing one flat face of the second substrate 5. Similarly, the second face 12 is configured as a flat face that can be disposed facing one flat face of the second substrate 5, and also as a flat face that can be disposed facing one flat face of the first substrate 4.

Note that reference character 16r denotes a connector guide face that is formed, for example, to have a curved surface shape. In the present embodiment, the connector guide face 16r is provided at the convex-portion end faces 16a and 16b, respectively.

As a result, the male connector 1m can be smoothly introduced between the connector abutting convex portions 16 on one inner face side and the connector abutting convex portions 16 on the other inner face side that have the distance Lp therebetween. As the male connector 1m is introduced, each connector abutting convex portion 16 elastically deforms smoothly from the first convex-portion end face 16a side or the second convex-portion end face 16b side.

Although the connector guide face 16r is formed in a curved surface shape, the connector guide face is not limited to a curved surface shape, and may be an inclined face, for example, a so-called "C-face" in which the gradient angle is 45 degrees.

As shown in FIG. 2A and FIG. 2B, the first sealing convex portion 14 is, for example, a semicircular convex portion that protrudes by a predetermined amount from the first face 11. The first sealing convex portion 14 is provided so as to surround the through-hole 13. The second sealing convex portion 15 is, for example, a semicircular convex portion that protrudes by a predetermined amount from the second face 12. The second sealing convex portion 15 is provided so as to surround the through-hole 13. The first sealing convex portion 14 and the second sealing convex portion 15 are formed in the same shape.

A height Hp from the distal end face of the first sealing convex portion 14 to the distal end face of the second sealing convex portion 15 is previously set to be larger than a connector height Hc in a connector-connected state in which the male connector 1m and the female connector 2f are electrically connected. In addition, an amount of collapse (also described as "rate of collapse") is set with respect to the sealing convex portions 14 and 15 so that the sealing convex portions 14 and 15 are crushed by a predetermined amount. The maximum amount of collapse of the first sealing convex portion 14 and the maximum amount of collapse of the second sealing convex portion 15 are equal, and are set to an amount t (see FIG. 5).

That is, in the present embodiment, the following relation is set between the heights Hp and Hc and the maximum amount of collapse t:

$$Hp-2t>Hc$$

Note that the respective sealing convex portions 14 and 15 are not limited to a semicircular convex portion, and as long as the maximum amount of collapse t can be obtained, the sealing convex portions 14 and 15 may be quadrangular convex portions or convex portions with a curved surface shape or the like.

According to the present configuration, for example, the male connector 1m and the female connector 2f that are electrically connected are housed in the through-hole 13 of the packing 3 in a state in which the first sealing convex portion 14 that has been crushed by one flat face of the first substrate 4 is adherently disposed on the one flat face of the first substrate 4, and the second sealing convex portion 15 that has been crushed by one flat face of the second substrate 5 is adherently disposed on the one flat face of the second substrate 5.

Note that in the present embodiment a width dimension W of the packing 3 is previously set to be larger than a width dimension of the second substrate 5. The packing 3 includes an exposed portion (see reference numeral 17 in FIG. 6) that is exposed from the second substrate 5. The exposed portion 17 is a notification portion, and the packing 3 is colored with a color that is different than at least the color of the second substrate 5.

In the present embodiment, the relationship between the color of the packing 3 and the color of the second substrate 5 is that of complementary colors, or the chroma of the packing 3 and the chroma of the second substrate 5 are different, with the chroma of the packing 3 being set to a higher value than the chroma of the second substrate 5.

The action of the connector mechanism 10 configured as described above will now be described referring to FIG. 3A to FIG. 6.

When connecting the first connector 1 mounted on the first substrate 4 and the second connector 2 mounted on the second substrate 5, first the packing 3 is attached to the first connector 1 of the first substrate 4.

At this time, a worker picks up the packing 3 using the worker's fingers and disposes the packing 3 on top of the first connector 1. Then, as shown by a broken line in FIG. 3B, for example, the first convex-portion end faces 16a of the connector abutting convex portions 16 are placed on top of the first connector 1 to enter a state in which the first convex-portion end faces 16a are disposed thereon. Reference character 1p denotes a connector pin.

Figure 3A:
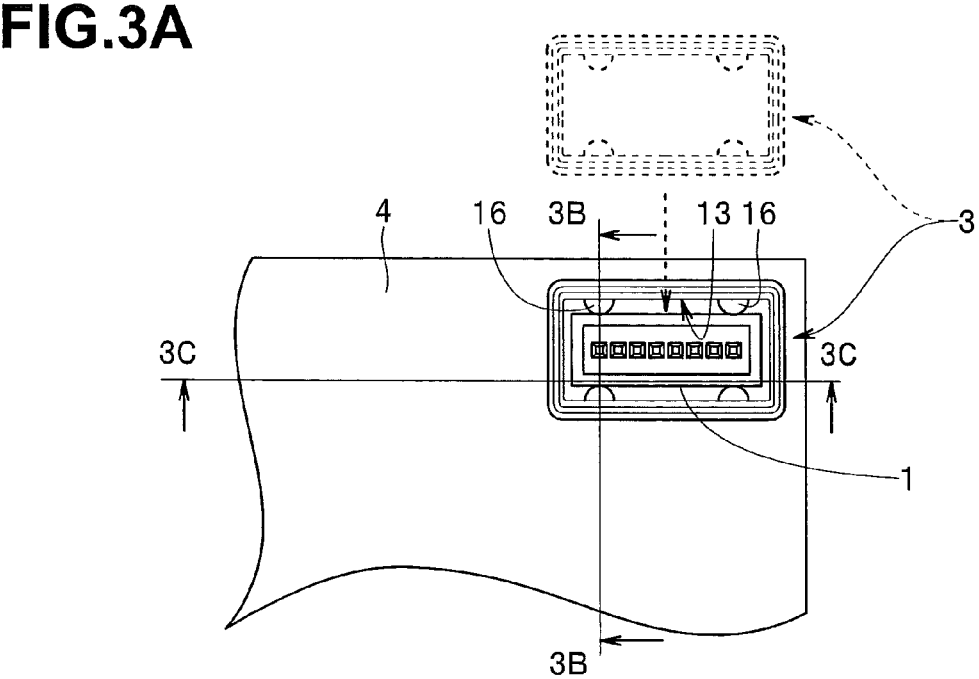
FIG. 3A is a view illustrating attachment of the packing to the connector.

Next, the worker pushes the packing 3 in the direction of the first substrate 4 against the elastic force of the connector abutting convex portions 16. Thereupon, the connector abutting convex portions 16 are elastically deformed gradually from the first convex-portion end face 16a side by the first connector 1. Thus, as shown in FIG. 3A to FIG. 3C, the packing 3 is attached to the outer face side of the first connector 1.

Figure 3B:
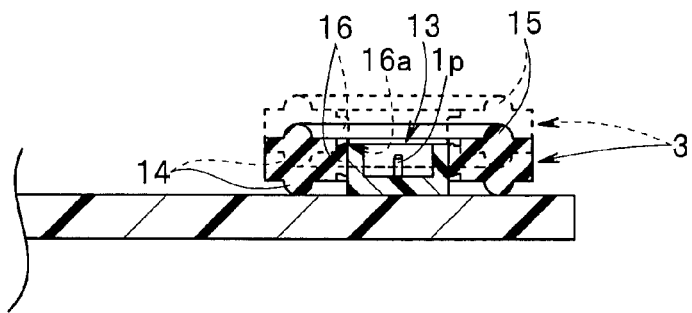
FIG. 3B is a cross-sectional view along a line 3B-3B indicated by arrows in FIG. 3A, which is a view illustrating a state in which the packing is disposed on the connector.
Figure 3C:
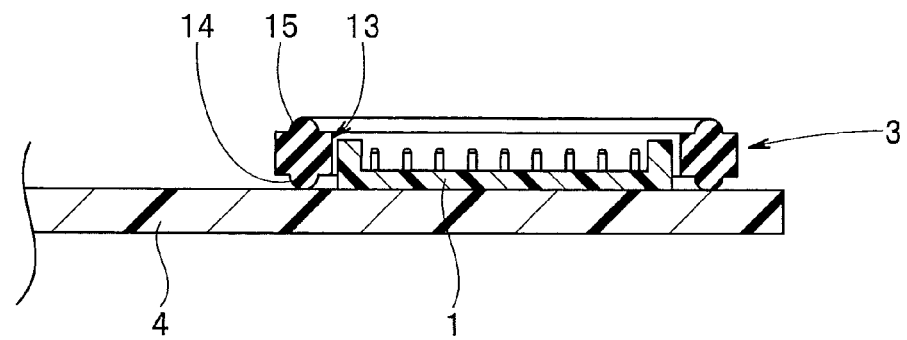
FIG. 3C is a cross-sectional view along a line 3C-3C indicated by arrows in FIG. 3A, which is a view illustrating a state in which the packing is disposed on the connector.

At this time, as shown in FIG. 3B, the connector abutting convex portions 16 of the packing 3 are crushed and adhere to the outer face of the first connector 1. As a result, the packing 3 is held by an elastic force on the outer face of the first connector 1. In this elastically held state, the packing 3 is held without dropping off from the first connector 1 by the elastic force of the connector abutting convex portions 16.

Figure 4:
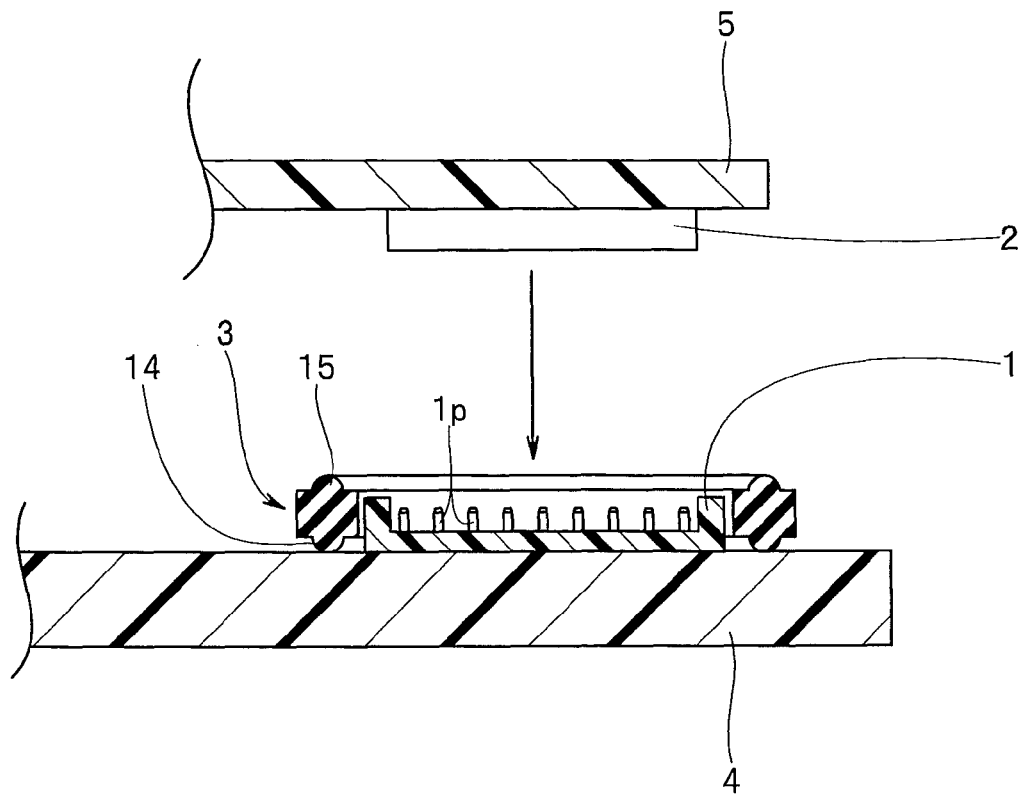
FIG. 4 is a view illustrating a state in which a connector of a second substrate is connected to a connector of a first substrate to which the packing is attached.

Next, as shown in FIG. 4, the worker performs work to connect the second connector 2, which is mounted on the second substrate 5, to the first connector 1, which is mounted on the first substrate 4 and to which the packing 3 is attached.

During the connection work, because the packing 3 is securely held by a predetermined elastic force on the outer face of the first connector 1, the worker can suitably adjust the orientation of the first substrate 4 and the orientation of the second substrate 5 and swiftly perform the connector connection work.

Upon starting the work to connect the first connector 1 and the second connector 2, first, a plurality of the connector pins 1p of the first connector 1 are guided into guide holes, which are not shown in the drawings, of the second connector 2. As a result, the space between the first substrate 4 and the second substrate 5 gradually narrows. The one flat face of the second substrate 5 then abuts against the second sealing convex portion 15.

Here, as the worker continues the connection work, the second sealing convex portion 15 is gradually crushed by one flat face of the second substrate 5, and the first sealing convex portion 14 that abuts against one flat face of the first substrate 4 is gradually crushed thereby. At this time, the worker proceeds with the work to connect the connectors against the elastic force of the sealing convex portions 14 and 15.

Figure 5:
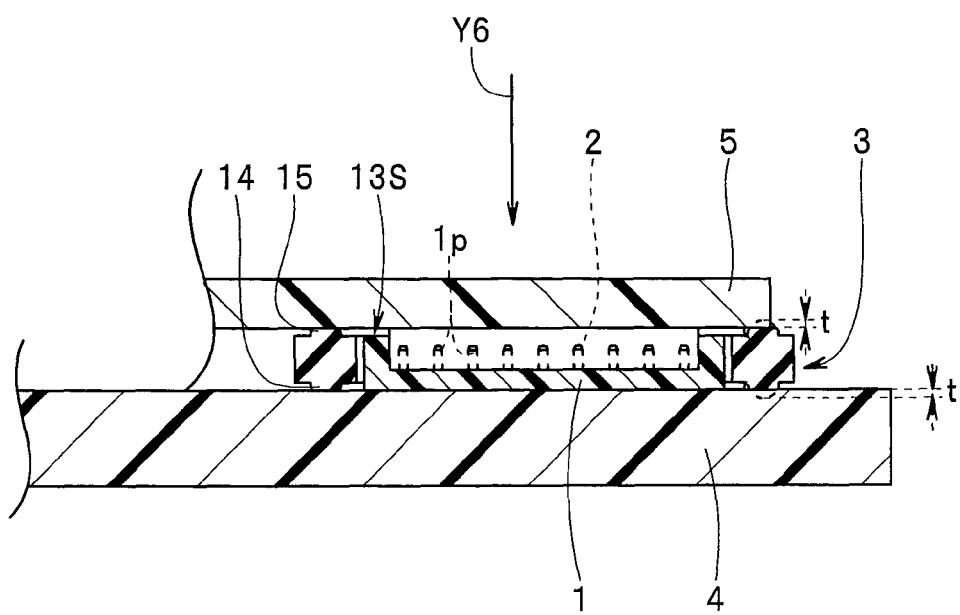
FIG. 5 is a view illustrating an action of the packing in a connector-connected state in which the connector of the first substrate and the connector of the second substrate are connected.

As a result, the first connector 1 and the second connector 2 enter a predetermined connector-connected state. The first connector 1 and the second connector 2 that are in the connector-connected state are, as shown in FIG. 5, housed and disposed in a water-tight manner inside a connector space 13S that is constituted by the first sealing convex portion 14 being adhered to the one flat face of the first substrate 4 and the second sealing convex portion 15 being adhered to the one flat face of the second substrate 5.

Figure 6:
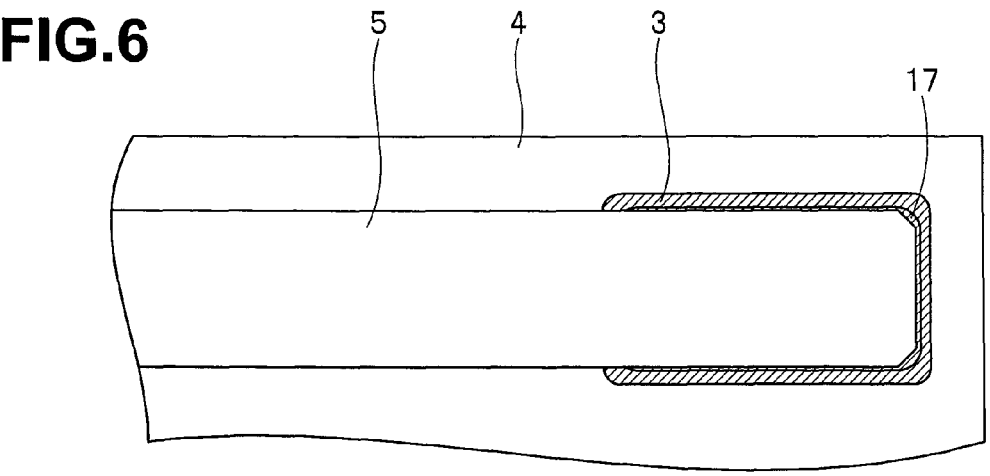
FIG. 6 is a top view of the connector-connected state, which is a view in which a connector connection portion is viewed from the direction of an arrow Y6 in FIG. 5.

At this time, as shown in FIG. 6, the exposed portion 17 of the packing 3 is exposed from the exterior of the second substrate 5. In the present embodiment, the first substrate 4 and the second substrate 5 are the same color, and the packing 3 is a different color to the substrates 4 and 5. For example, the packing 3 and the substrates 4 and 5 are colored so as to be in a complementary color relationship to each other.

Note that the aforementioned predetermined connector-connected state is a connected state in which the connectors 1p of the male connector 1m are electrically connected with terminals of the female connector 2f, and the male connector 1m and the female connector 2f are integrally attached without dropping out. The elastic force of the sealing convex portions 14 and 15 is a force in a direction that causes the male connector 1m to withdraw from the female connector 2f. However, the elastic force of the sealing convex portions 14 and 15 is set in consideration of an attaching force that integrally attaches the male connector 1m and the female connector 2f to each other. That is, the elastic force of the plurality of sealing convex portions 14 and 15 does not constitute an obstacle to the connector connection between the male connector 1m and the female connector 2f.

Thus, the connector abutting convex portions 16 for which the amount of collapse is previously set are provided on the inner face of the packing 3. As a result, the worker can easily attach the packing 3 to the connectors. Further, after the packing 3 is attached to the connectors, the packing 3 can be disposed in a state in which the packing 3 is stably retained on the outer faces of the connectors by the elastic force of the connector abutting convex portions 16. Thus, a problem that arises due to the packing falling off is resolved.

The distance La from the first convex-portion end face 16a of the connector abutting convex portion 16 provided in the packing 3 to the first face 11 and the distance Lb from the second convex-portion end face 16b to the second face 12 are set to equal distances. Consequently, when attaching the packing 3 to the connectors, the worker can perform the attaching work without needing to pay attention to whether the worker is handling the top or bottom of the packing 3.

Further, the sealing convex portions 14 and 15 are provided so as to surround the through-hole 13 on the first face 11 and the second face 12, respectively, of the packing 3. As a result, by adherently disposing the sealing convex portions 14 and 15 on one face of the first substrate 4 and one face of the second substrate 5, respectively, the through-hole 13 of the packing 3 can be constituted as the connector space 13S that is watertight.

In addition, the relationship Hp−2t>Hc is set with respect to the height Hp from the distal end face of the first sealing convex portion 14 to the distal end face of the second sealing convex portion 15, the connector height Hc in the connector-connected state, and the maximum amount of collapse t of the sealing convex portions 14 and 15. Consequently, the first connector 1 and the second connector 2 in the connector-connected state can be housed and disposed in the connector space 13S.

The width dimension of the packing 3 is set to a wider width than the width dimension of the second substrate 5, and the color of the packing 3 is set to a different color than the color of the second substrate 5. Consequently, it is possible to easily check visually whether or not the packing 3 is attached to the connector. Accordingly, a problem that arises due to packing not being attached to the connector can be resolved.

Note that in the above described embodiment, a configuration is adopted in which the first sealing convex portion 14 that protrudes with respect to the first face 11 of the packing 3 is caused to elastically abut against one flat face of the first substrate 4 or one flat face of the second substrate 5, and the second sealing convex portion 15 that protrudes with respect to the second face 12 is caused to elastically abut against one flat face of the second substrate 5 or one flat face of the first substrate 4.

However, a configuration may also be adopted in which the first sealing convex portion 14 and the second sealing convex portion 15 are not provided in the packing 3, and the first face 11 is caused to elastically abut against one flat face of the first substrate 4 or one flat face of the second substrate 5, and the second face 12 is caused to elastically abut against one flat face of the second substrate 5 or one flat face of the first substrate 4. As a result, substantially the same actions and effects as those of the above described packing 3 can be obtained.

Figure 7:
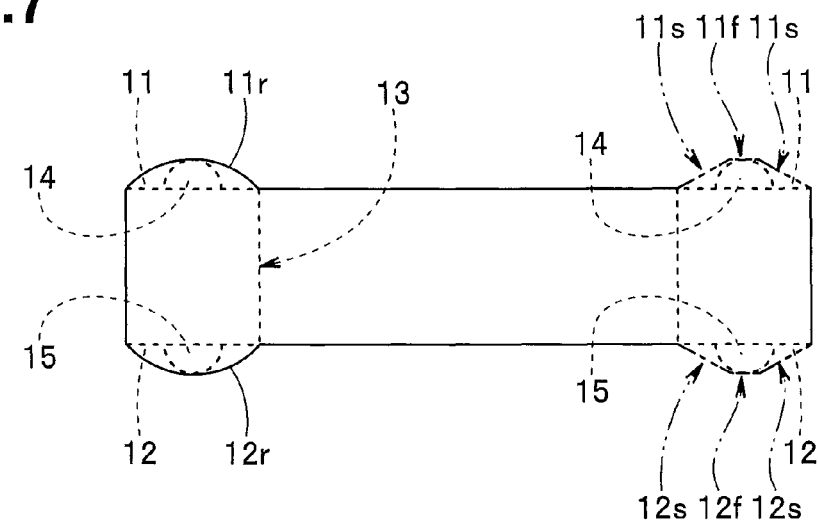
FIG. 7 is a view illustrating another configuration of the packing.

Note that, with respect to this configuration, as shown by solid lines in FIG. 7, a configuration may also be adopted in which the first face 11 is formed as a curved face 11r and the second face 12 is formed as a curved face 12r, or as shown by alternate long and two short dashes lines, the first face 11 is configured to include an inclined face 11s and a flat face 11f, and the second face 12 is configured to include an inclined face 12s and a flat face 12f.

Figure 8:
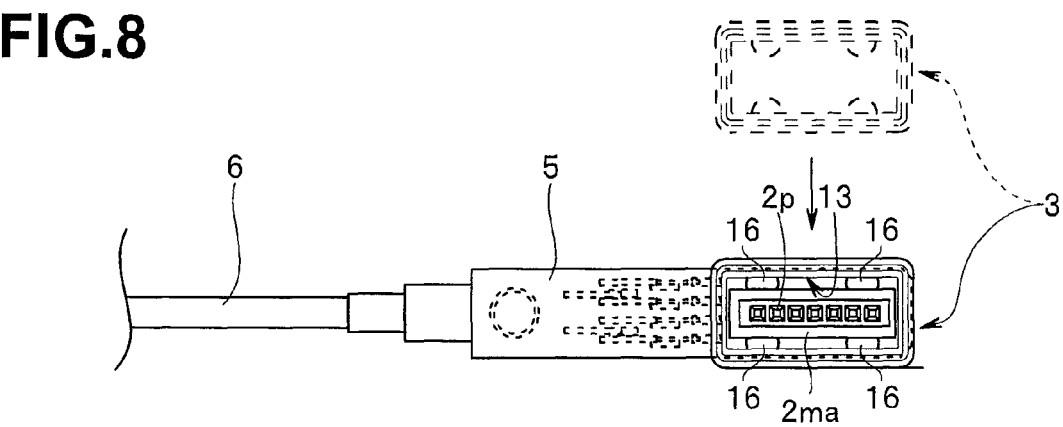
FIG. 8 is a view illustrating a configuration in which the packing is disposed on the connector that is mounted on the second substrate.

Further, in the above described embodiment, a configuration is adopted in which the connector abutting convex portions 16 that are protrusively provided on the inner face of the packing 3 are pushed against the outer face of the first connector 1 by an elastic force. However, in a case where the second connector 2 mounted on the second substrate 5 is a male connector, as shown in FIG. 8, connector connection work can be performed in which the packing 3 is attached by means of an elastic force of the connector abutting convex portions 16 to the outer face of a male connector 2ma that is mounted on the second substrate 5. Reference character 2p denotes a connector pin.

In addition, in the above described embodiment, a through-hole cross-sectional shape in a direction that is orthogonal to the axis of the through-hole is a rectangular shape. However, the through-hole cross-sectional shape is not limited to a rectangular shape, and as long as the shape is similar to the outer shape of the connector, the through-hole cross-sectional shape may be a square shape or a circular shape. When a configuration is adopted in which the through-hole cross-sectional shape is a circular shape, the plurality of connector abutting convex portions are provided at regular intervals in the circumferential direction with respect to the inner circumferential face of the circular shaped through-hole.

Note that in the foregoing embodiment a configuration is adopted in which the second substrate 5 is electrically connected to one end of the signal wire 6. However, the second substrate 5 is not limited to a configuration in which the second substrate 5 is electrically connected to one end of the signal wire 6.

What is claimed is:

1. A connector mechanism, comprising:
 a first connector that is arranged on one flat face of a first substrate;
 a second connector that is arranged on one flat face of a second substrate and is electrically connected to the first connector in a positional relationship in which the one flat face of the second substrate and the one flat face of the first substrate face each other; and
 a packing having: a first face that elastically abuts against the one flat face of the first substrate; a second face that is a face on an opposite side to the first face and that elastically abuts against the one flat face of the second substrate; and a plurality of connector abutting convex portions that are protrusively provided with respect to an inner face of a connector space that is a through-hole which allows the first face and the second face to communicate and sealingly houses the connectors in a connected state, and that elastically abut against an outer face of the connectors disposed in the connector space and are disposed integrally with the connectors.

2. The connector mechanism according to claim 1, wherein:
 the packing further comprises a first sealing convex portion that is provided in a protruding manner with respect to the first face and elastically abuts against the one flat face of the first substrate, and a second sealing convex portion that is provided in a protruding manner with respect to the second face and elastically abuts against the one flat face of the second substrate.

3. The connector mechanism according to claim 2, wherein:
in a state in which the first sealing convex portion elastically adheres to the one flat face of the first substrate, and the second sealing convex portion elastically adheres to the one flat face of the second substrate,
a distance from the one flat face of the first substrate to the one flat face of the second substrate is larger by a predetermined dimension than a distance from the first face to the second face of the packing.

4. The connector mechanism according to claim 1, wherein:
the connector abutting convex portions that protrude with respect to the inner face of the connector space comprise a first convex-portion end face that forms an end face on the first face side and a second convex-portion end face that forms an end face on the second face side;
the first convex-portion end face is provided at a position that is separated by a predetermined distance from the first face of the packing;
the second convex-portion end face is provided at a position that is separated by a predetermined distance from the second face of the packing; and
a distance from the first face to the first convex-portion end face and a distance from the second face to the second convex-portion end face are equal.

5. The connector mechanism according to claim 4, wherein:
an inner face shape of the connector space is a similar shape to an outer shape of the connectors disposed in the connector space, and
when the outer shape of the connectors is a rectangular shape, the connector abutting convex portions are provided in a positional relationship in which the connector abutting convex portions face each other at least in a one-to-one relationship in the connector space.

6. The connector mechanism according to claim 5, wherein:
the connector abutting convex portions are provided in a positional relationship in which the connector abutting convex portions face each other at least in a one-to-one relationship in a longitudinal direction of the connector space.

7. The connector mechanism according to claim 4, wherein:
when an outer shape of the connectors is a circular shape, the connector abutting convex portions are provided at regular intervals with respect to a circumferential direction on an inner circumferential face of the connector space.

8. The connector mechanism according to claim 1, wherein:
in a state in which the first face or the first sealing convex portion elastically adheres to the one flat face of the first substrate, and the second face or the second sealing convex portion elastically adheres to the one flat face of the second substrate,
the first face or the second face of the packing has an exposed portion that is exposed to an outside from one of the first substrate and the second substrate.

9. The connector mechanism according to claim 8, wherein:
the exposed portion is a notification portion that notifies whether or not the packing is attached to the connectors, and the exposed portion is colored with a color that is different than a color of a substrate that is exposed.

* * * * *